(12) United States Patent
Berra

(10) Patent No.: US 7,318,835 B2
(45) Date of Patent: Jan. 15, 2008

(54) ENDOLUMINAL PROSTHESIS HAVING EXPANDABLE GRAFT SECTIONS

(75) Inventor: Humberto Berra, Cooper City, FL (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 230 days.

(21) Appl. No.: 11/181,384

(22) Filed: Jul. 13, 2005

(65) Prior Publication Data

US 2006/0030926 A1 Feb. 9, 2006

Related U.S. Application Data

(60) Provisional application No. 60/589,260, filed on Jul. 20, 2004.

(51) Int. Cl.
*A61F 2/06* (2006.01)
(52) U.S. Cl. ..................................... 623/1.12
(58) Field of Classification Search ....... 623/1.27–1.34
See application file for complete search history.

(56) References Cited

U.S. PATENT DOCUMENTS

| | | | |
|---|---|---|---|
| 5,713,917 A | 2/1998 | Leonhardt et al. | |
| 5,824,042 A * | 10/1998 | Lombardi et al. | 623/1.13 |
| 6,193,745 B1 | 2/2001 | Fogarty et al. | |
| 6,344,052 B1 | 2/2002 | Greenan et al. | |
| 6,773,457 B2 * | 8/2004 | Ivancev et al. | 623/1.28 |
| 6,974,471 B2 * | 12/2005 | Van Schie et al. | 623/1.12 |
| 7,105,202 B2 * | 9/2006 | Okamoto et al. | 427/238 |
| 7,189,255 B2 * | 3/2007 | DePalma | 623/1.13 |
| 2003/0088305 A1 * | 5/2003 | Van Schie et al. | 623/1.12 |
| 2004/0019375 A1 | 1/2004 | Casey et al. | |

FOREIGN PATENT DOCUMENTS

| | | |
|---|---|---|
| WO | WO03/034948 | 5/2003 |
| WO | WO03/051232 | 6/2003 |
| WO | WO2006/020222 | 2/2006 |

* cited by examiner

*Primary Examiner*—Suzette Gherbi
(74) *Attorney, Agent, or Firm*—Forrest Gunnison

(57) ABSTRACT

An endoluminal prosthesis comprises a tubular member having a proximal opening and a distal opening providing a lumen through which body fluids may flow. The tubular member is constructed of a graft material. The tubular graft is formed of a first material such as a woven fiber or other suitable material for conducting fluid, and sections of a second material configured to extend or contract to permit the tubular graft to flex or straighten to conform to the anatomy in which it is deployed.

10 Claims, 3 Drawing Sheets

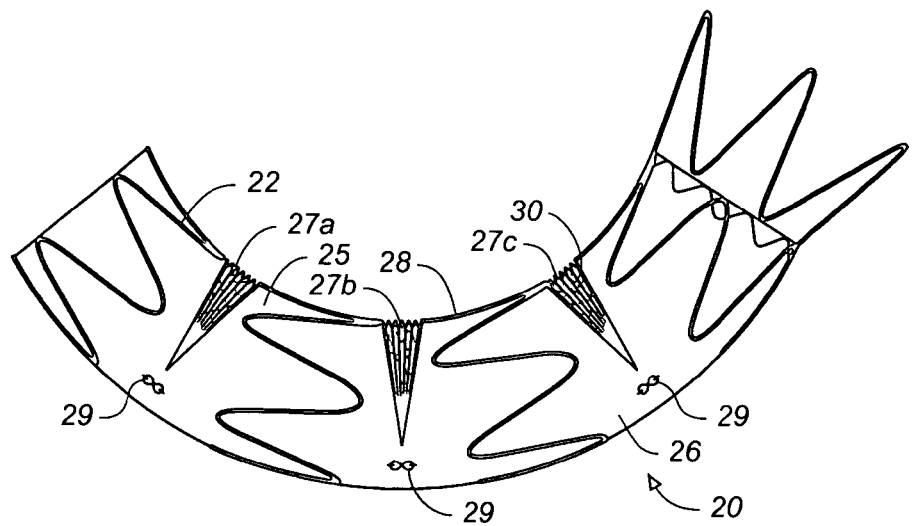
FIG._1
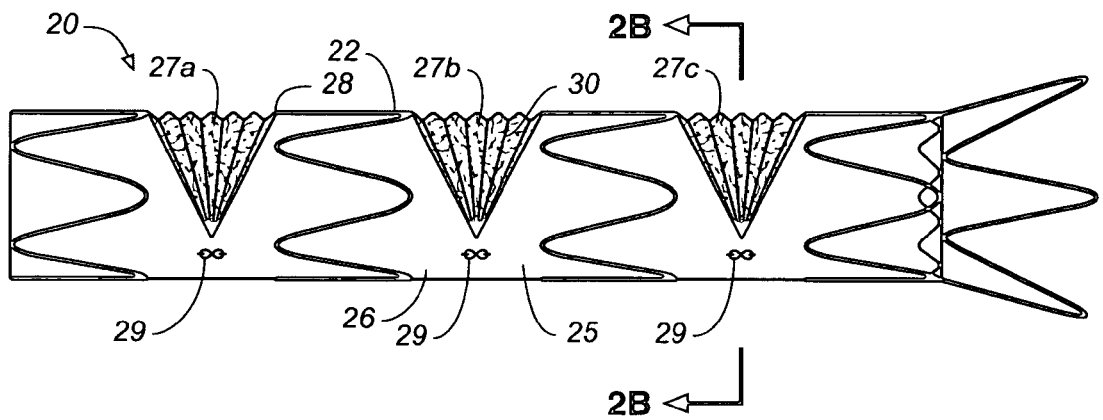
FIG._2A
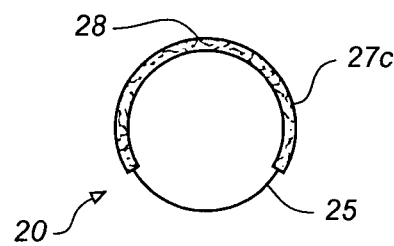
FIG._2B

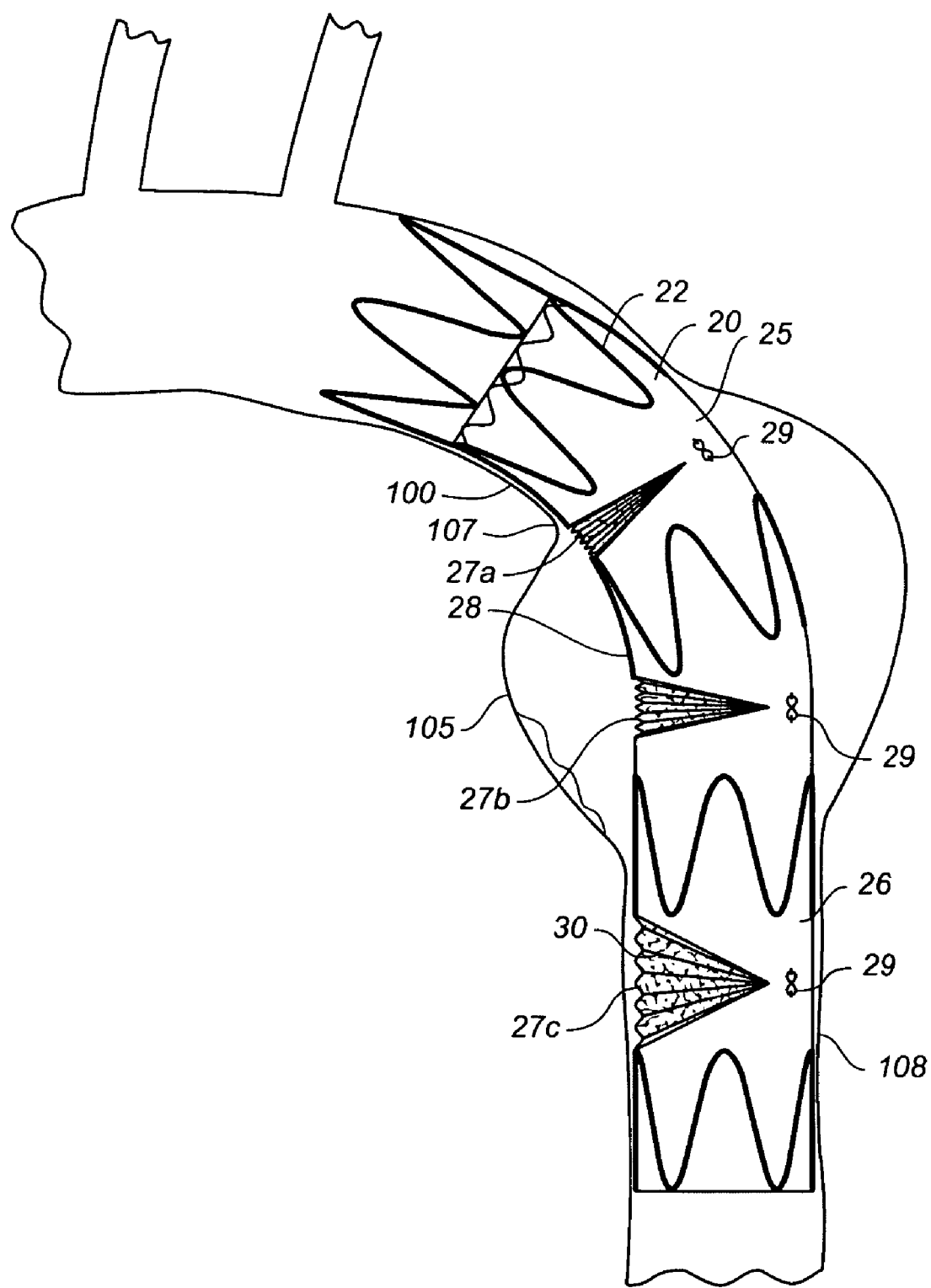
FIG._3

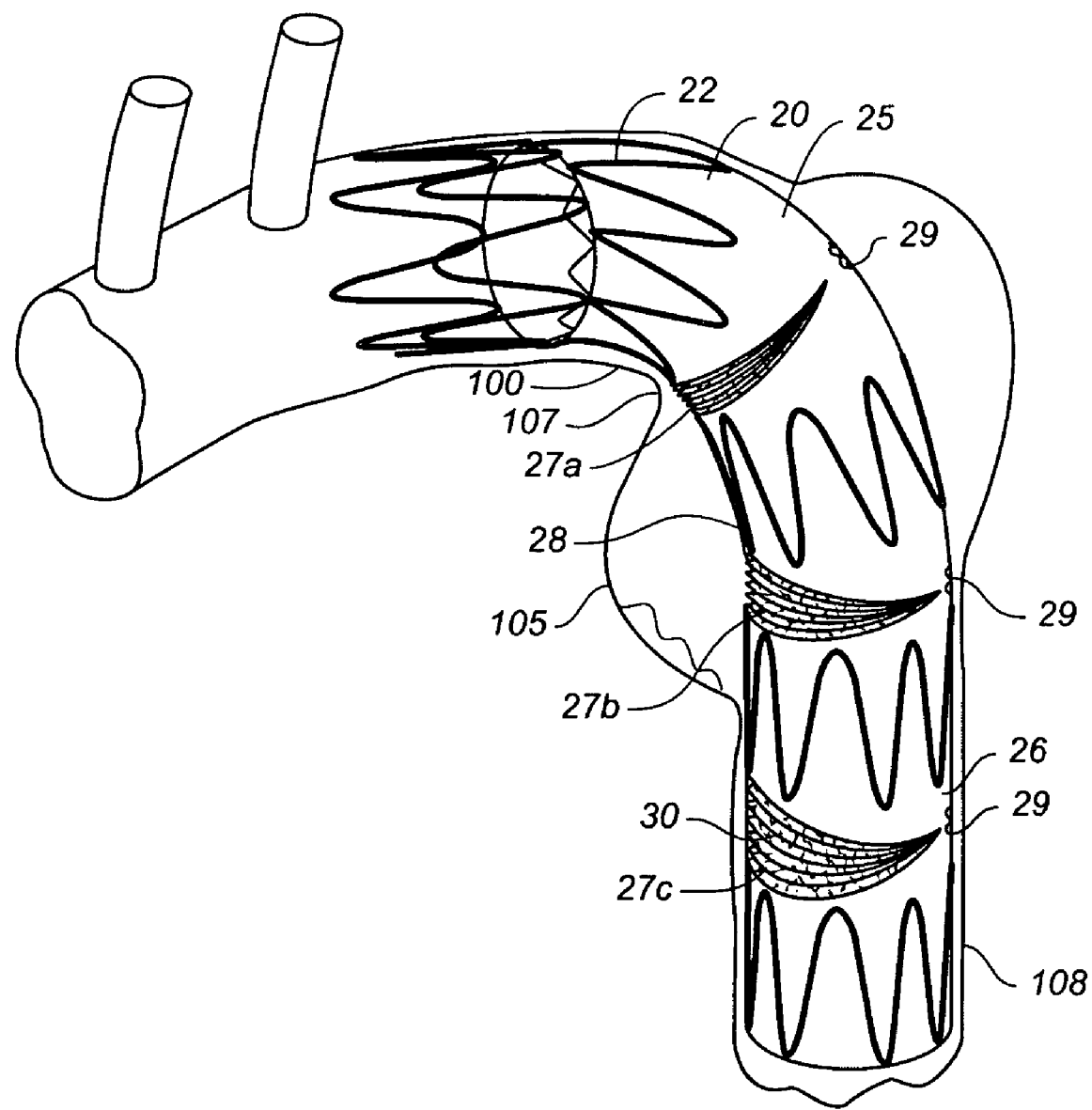
FIG._4

ENDOLUMINAL PROSTHESIS HAVING EXPANDABLE GRAFT SECTIONS

RELATED FIELD

1. Field of the Invention

The present invention relates to tubular prostheses such as grafts and endoluminal prostheses including, for example, stent-grafts and aneurysm exclusion devices, and methods for placement of such grafts and endoluminal structures. More particularly, the present invention relates to an improved a tubular graft for placement within or in place of a body lumen. The present invention further relates to an endoluminal prosthesis of particular utility in treating vessels with particularly curved or tortuous anatomies.

2. Background of the Invention

A wide range of medical treatments have been previously developed using "endoluminal prostheses," which terms are herein intended to mean medical devices that are adapted for temporary or permanent implantation within a body lumen, including both naturally occurring and artificially made lumens. Examples of lumens in which endoluminal prostheses may be implanted include, without limitation: arteries such as those located within coronary, mesentery, peripheral, or cerebral vasculature; veins; gastrointestinal tract; biliary tract; urethra; trachea; hepatic shunts; and fallopian tubes. Various types of endoluminal prostheses have also been developed, each providing a uniquely beneficial structure to modify the mechanics of the targeted luminal wall.

A number of vascular devices have been developed for replacing, supplementing or excluding portions of blood vessels. These vascular grafts may include but are not limited to endoluminal vascular prostheses and stent grafts, for example, aneurysm exclusion devices such as those used in the thoracic aortic aneurysm ("TAA") and abdominal aortic aneurysm ("AAA") are used to exclude aneurysms and provide a prosthetic lumen for the flow of blood. One very significant use for endoluminal or vascular prostheses is in treating such aneurysms. Vascular aneurysms are the result of abnormal dilation of a blood vessel, usually resulting from disease or a genetic predisposition, which can weaken the arterial wall and allow it to expand. While aneurysms can occur in any blood vessel, most occur in the aorta and particularly the abdominal and thoracic aorta and peripheral arteries.

Aneurysms have been most commonly treated in open surgery procedures where the diseased vessel segment is bypassed and repaired with an artificial vascular graft. While considered to be an effective surgical technique in view of the alternative of a fatal ruptured abdominal aortic aneurysm, the open surgical technique suffers from a number of disadvantages. The surgical procedure is complex and sometimes requires long hospital stays due to serious complications and has long recovery times and high mortality rates. To reduce the mortality rates, complications and duration of hospital stays, less invasive devices and techniques have been developed. The improved devices include tubular prostheses that provide an artificial lumen or lumens for blood flow while excluding blood flow to the aneurysm site in the native lumen. They are introduced into the blood vessel using a catheter in a less or minimally invasive technique. Although frequently referred to as stent-grafts, these devices differ from covered stents in that they are not used to mechanically prop open natural blood vessels. Rather, they are used to secure an artificial lumen in a sealing engagement with the vessel wall without further opening the natural blood vessel that is already abnormally dilated.

Typically, these endoluminal prostheses or stent grafts are constructed of a graft material, such as woven polymer materials (e.g., —Dacron(polyester), or polytetrafluoroethylene ("PTFE"), and a support structure. The stent-grafts typically have graft material secured onto the inner diameter or outer diameter of the support structure that supports the graft material and/or holds it in place against a luminal wall. The prosthesis is typically secured to a vessel wall upstream and downstream of the aneurysm site spanning the aneurysm with at least one attached expandable annular spring member that provides sufficient radial force so that the prosthesis engages the inner lumen wall of the body lumen to seal the prosthetic lumen from the aneurysm. In other devices, other mechanisms have also been used to engage the vessel walls such as, for example, forcibly expandable members or hook like members that puncture the vessel wall.

When placing a stent graft in a curved or tortuous vessel, the graft material tends to wrinkle or kink where the stent graft bends to conform to the shape of the vessel. Kinking is understood to be a predefined reducing in the flow area of the internal lumen, obstructing the flow lumen and creating a potentially thrombus generating location. Quantitatively, reductions in area of 25% or greater of the total straight tube flow area can be considered kinked. Kinking is particularly of concern in thoracic applications where the aorta tends to curve as in the aortic arch.

Accordingly it would be desirable to provide a device structure that avoids such wrinkling and kinking in curved vessels.

SUMMARY OF THE INVENTION

The present invention provides an endoluminal prosthesis having a tubular graft, configured to bend without substantial kinking when deployed in a curved lumen.

An embodiment of the endoluminal prosthesis according to the invention comprises a tubular member having a proximal opening and a distal opening providing a lumen through which body fluids may flow. The tubular member is constructed of a graft material and typically at least one annular support member. The tubular graft is formed of a first material such as a woven fiber or other suitable material for conducting fluid, and sections of a second material constructed or configured to expand or contract to permit the tubular graft to flex (i.e., curve) or straighten to conform to the anatomy in which it is deployed while not substantially obstructing or impeding the flow of blood as a kink or other bend in a standard stent graft would. In one variation, the sections of elastic material are provided in side locations of the prosthesis that are stretched when the device is straight and that contract or compress when deployed in a curved position to permit bending of the prosthesis while reducing or minimizing the kinking and wrinkling typically found in such endoluminal prostheses.

In general, the endoluminal prosthesis is radially compressed, and loaded on or otherwise coupled to, the distal end of a catheter for delivery to the deployment site. The deployment/treatment site is located using an imaging technique such as fluoroscopy and is guided through the vasculature with the use of a guide wire to the treatment site. The device has radiopaque markers that indicate the orientation or rotational-angular position of the device when located in the catheter. The device is properly oriented for deployment when the catheter is positioned so that the side having the elastic sections is located adjacent the arcuate side of the vessel having a smaller radius curvature. Once properly located for deployment, any restraining mechanism or protective sheath covering is retracted from the tubular graft. The annular support members and the tubular graft are then released, thus allowing the annular springs to expand, and attach or engage the tubular member to the inner wall of the body lumen. Where the vasculature is curved, the expandable members tend to return to the compressed or contracted position so that the tubular graft tends to curve at those locations. Where the vasculature is straighter, the sections of elastic material are forced by the shape of the vasculature to maintain their shape present in the catheter, i.e., the expandable sections tend to expanded or opened up.

BRIEF DESCRIPTION OF THE DRAWINGS

FIG. 1 is a side view of a curved endoluminal prosthesis according to the invention.

FIG. 2A is a side view of the endoluminal prosthesis of FIG. 1 straightened out.

FIG. 2B is a cross-section of the endoluminal prosthesis of FIG. 2A along the lines 2B-2B.

FIG. 3 is a side view of the endoluminal prosthesis of FIG. 1 deployed across an aortic aneurysm.

FIG. 4 is a perspective view of the endoluminal prosthesis of FIG. 3.

DETAILED DESCRIPTION

Referring to FIGS. 1 and 2A-2B, a prosthesis 20 of an embodiment is illustrated in which the graft is constructed to conform the prosthesis to the anatomy of a body lumen in which it is deployed with an expandable section or sections of graft material. The prosthesis 20 comprises a tubular graft 25 and a series of radially compressible annular support members 22 attached to tubular graft 25. The annular support members 22 support the graft and/or bias the prosthesis 20 into conforming fixed engagement with an interior surface of an aorta 100 (See FIGS. 3 and 4). The annular support members 22 are spring members having predetermined radii and are constructed of a material such as Nitinol in a superelastic, shape set condition.

The tubular graft 25 comprises a main tubular portion 26 and a series of expandable graft portions or sections 27a-c located on a semi-cylindrical portion 28 (as defined herein a semi-cylindrical portion is not limited to one half of the circular circumference of the tube to be curved—since the graft material on the outside of the curve in which the stent graft is to be placed, does not stretch (at all) a section of flexible material needs to reach to at least half way around the circumference, but more likely ⅔ to ¾ to ⅞ around the circumference—all of which configurations might be termed a semi-cylindrical portion or half or more, but less than all the way around, or less than 90% of the way around.), along a length of the tubular graft 25. The expandable portions 27a-c wrap around or are formed around a semi-cylindrical portion 28 of the tubular prosthesis 20 as illustrated in FIG. 2B.

The expandable portions 27a-c of the tubular graft 25 are relatively unsupported by annular support members (i.e. they are not directly supported by support members e.g., are not attached to the graft material of the expandable portions) and the sections are relatively flexible (i.e., more flexible than the main tubular portion 26 of the tubular graft). The main tubular portion 26 is formed of a first biocompatible, low-porosity woven fabric, such as a woven polyester or Dacron. Where a Talent™ Stent Graft is used, the principal stent graft material is a thin woven monofilament, which is considered to be relatively stiff and creates indentations or kinks that reduce the area of the flow lumen as a tubular graft of the material is formed into an arch shape. A description of the monofilament material can be found in U.S. Pat. No. 6,344,052 to Greenan et al., incorporated herein by reference. The series of expandable portions 27a-c are formed of a soft corrugated woven Dacron (e.g. Cooley™ VeriSoft™ material) having corrugated folds 30 oriented in a circumferential pattern that are sewn onto the main portion 26 of the tubular graft 25. The corrugated folds 30 may be formed by placing the material on a mandrel and winding a wire around the tube of material. (For example, a tube of material may be placed around a mandrel, the folds formed, and then section may be cut to create the expandable portion sections.) Thus, the corrugated material acts like an accordion to expand and contract. The graft materials are thin-walled so that the prosthesis may be compressed into a small diameter, yet are capable of acting as a strong, leak-resistant fluid conduit when expanded to a cylindrical tubular form.

The expandable portions 27a-c when expanded (FIG. 2A) have a larger triangular or wedge shaped profile (as viewed from the side as illustrated in FIG. 2A). Conversely, when the expandable portions 27a-c are compressed, closing the folds, have a smaller triangular or wedge shaped profile (as viewed from the side as illustrated in FIG. 1). When expanded (straightened) as illustrated in FIG. 2A, the expandable portions 27a-c expand to support the side of the semicircular side portion 28 of the tubular graft 25. The flexibility/foldability of the expandable portions 27a-c permit the prosthesis 20 to concentrate the wall compression in those regions and allow the stent graft to bend or curve with reduced kinking, as compared to a uniform graft material wall configuration stent graft, such as the Talent™ Stent Graft. When the expandable portions 27a-c are compressed, closing the folds, creating a curve by reducing the length of the prosthesis along the semi-cylindrical portion 28 of the tubular graft 25.

In this embodiment, the annular support members 22 are sewn on to the outside of the tubular graft 25 by sutures. Alternative mechanisms of attachment may be used (such as embedding or winding within material, adhesives, staples or other mechanical connectors) and the annular support members 22 may be attached to the inside of the tubular graft 25. The support members 22 comprise a series of undulating ring members.

In FIGS. 3 and 4, the prosthesis 20 is shown in place in a thoracic aorta 100 excluding or bypassing, a diseased region 105 where the vessel wall is weakened and expanded. The prosthesis 20 is used to relieve blood pressure against the weakened vessel wall, by acting as a fluid conduit through the weakened diseased region 105 or aneurysm. In its deployed configuration, prosthesis 20 defines a conduit for blood flow through the aorta 100. When deployed, the annular support members 22 are designed to exert a radially outward force sufficient to bias the tubular graft 25 of the endoluminal prosthesis 20 into conforming fixed engagement with the interior surface of aorta 100 upstream and downstream of the diseased region 105. When deployed, the expandable portions 27a-c will permit the tubular graft 25 to bend or flex (contract or extent, or curve or straighten) as is necessary for the graft material to conform to the shape of the vessel and to thereby reduce kinking where the vessel curves.

As illustrated in FIGS. 3 and 4, expandable section 27a and 27b are compressed to permit the graft 25 to curve at a smaller radius curved portion 107 of the aorta 100 while section 27c is extended, i.e., open, permitting the graft 25 to conform to the straight portion 108. The annular members 22 also act to support the tubular graft 25, and/or to provide a leak resistant seal between the prosthesis 20 and the inner wall of the aorta 100.

To deploy the prosthesis 20, the prosthesis 20 is loaded into a catheter (not shown) in a straight position wherein the expandable portions 27a-c are expanded and annular support members 22 are held in a radially compressed configuration. A thin flexible sheath or cover (not shown) is placed over the prosthesis 20 to restrain the prosthesis and prevent it from damaging or catching on the luminal wall as it is delivered to the aneurysm site. The prosthesis 20 is delivered in a radially compressed state via the catheter through a surgically accessed vasculature, to the desired deployment site. When the distal end of the catheter is located at the deployment site the cover is retracted in a manner as is well understood by persons skilled in the art. The tubular graft 25 further includes radiopaque markers 29 that are sewn into the graft material at predetermined locations with respect to the expandable portions 27a-c and the semi-cylindrical portion 28 so that prior to deployment, the prosthesis 20 can be oriented under imaging, so that the semi-cylindrical portion 28 is aligned with the smaller radius curved portion 107 of the vessel. The annular support members 22 expand to bias the prosthesis into conforming fixed engagement with an interior surface of the vessel and engage the vessel wall upstream and downstream of the aneurysm site or diseased portion 105. The expandable sections 27a-c either expand or contract to flexibly conform to the anatomy of the vessel. The expanding and contracting may for example be by folding and unfolding a corrugated section, or by stretching or relaxing the material.

Surgical methods and apparatus for accessing the surgical site are generally known in the art and may be used to place the catheter within the vasculature and deliver the prosthesis to the deployment site. Additionally, various actuation mechanisms for retracting sheaths and where desired, inflating balloons of balloon catheters are known in the art. The prosthesis may be delivered to the deployment site by one of several ways. A surgical cut down may be made to access the femoral artery. The catheter is then inserted into the artery and guided to the aneurysm site using fluoroscopic imaging where the device is then deployed. The annular support members supporting the graft, biased in a radially outward direction, are released to expand and engage the prosthesis in the vessel against the vessel wall to provide an artificial lumen for the flow of blood. Another technique includes percutaneously accessing the blood vessel for catheter delivery, i.e., without a surgical cutdown. An example of such a technique is set forth in U.S. Pat. No. 5,713,917, incorporated herein by reference.

In this embodiment, the graft curves along one side of the length of the graft. However, the graft can be designed to fit other vessels of varying curvatures and twists by placing the expandable sections on a portion of a length of a side of a graft that would match the curvature of a corresponding portion vessel. Furthermore, the expandable sections may be constructed so that their ranges of expansion provide an curved portion for the greater arced side of a length of the graft when expanded, i.e., when contracted the sections provide a curve in one orientation or direction and when substantially expanded, provide a curve in the opposite orientation. (i.e., locating the expandable portion at the greater arced portion of a curved vessel). The device can also be custom made to fit the curvature of a vessel of a particular patient and can also create, e.g., folds that open on varying angles and/or that are positioned at varying locations about the circumference of the graft and along its length.

While the invention has been described with reference to particular embodiments, it will be understood to one skilled in the art that variations and modifications may be made in form and detail without departing from the spirit and scope of the invention.

The invention claimed is:

1. An endoluminal prosthesis to provide a lumen for the flow of body fluid therethrough, the endoluminal prosthesis comprising:
   a tubular graft comprising a graft material forming a lumen for the flow of body fluid therethrough; and
   at least one annular support member coupled to the graft material for supporting the graft material;
   wherein the graft material comprises a first graft material and at least one section of a second graft material attached to the first graft material, wherein the second graft material is different from the first graft material; the prosthesis comprises a semi-cylindrical portion configured to curve to define a smaller curved portion of the prosthesis; and wherein the at least one section of the second graft material is located on said semi-cylindrical portion and the second graft material is configured to bend to form the smaller curved portion without obstructing the lumen for the flow of body fluid.

2. The endoluminal prosthesis of claim 1 wherein the second graft material is a corrugated material.

3. The endoluminal prosthesis of claim 1, wherein the tubular graft comprises an unsupported portion, and wherein the unsupported portion comprises at least a portion of the at least one section.

4. The endoluminal prosthesis of claim 1 wherein the at least one section comprises a plurality of sections.

5. The endoluminal prosthesis of claim 1 wherein the at least one section of the second graft material comprises a plurality of sections located on the semi-cylindrical portion.

6. The endoluminal prosthesis of claim 1 further comprising a marker affixed to the prosthesis at a predetermined location with respect to the at least one section to identify the angular position of the prosthesis using an imaging system when the prosthesis is being deployed.

7. A method of conforming an endoluminal prosthesis to the anatomical curvatures of a body lumen comprising the steps of:
   providing an endoluminal prosthesis comprising:
      a tubular graft comprising a graft material forming a lumen for the flow of body fluid therethrough wherein the graft material comprises a first graft material and at least one section of a second graft material coupled to the first graft material wherein the second graft material is different from the first graft material; the at least one section of a second graft material comprises a semi-cylindrical portion configured to curve to define a smaller curved portion of the prosthesis; and wherein the at least one section of the second graft material is located on said semi-cylindrical portion and the second graft material is configured to bend to form the smaller curved portion without obstructing the lumen for the flow of body fluid;
   delivering the endoluminal prosthesis within a body lumen to a treatment site; and deploying the prosthesis so second graft material curves or straightens to conform to the curvature of the vessel without obstructing flow of blood through the lumen.

8. The method of claim 7 wherein the step of deploying the prosthesis comprises locating the second graft material adjacent a curved portion of a vessel so that the second graft material contracts to permit the prosthesis to conform to the anatomy of the body lumen.

9. The method of claim 7 wherein the step of deploying the prosthesis comprises deploying the second graft material adjacent a straight portion whereby the second graft material expands to permit the prosthesis to conform to the straight portion.

10. The method of claim 7 wherein the step of deploying the prosthesis comprises changing a length of a side of the prosthesis by releasing the prosthesis and allowing the second graft material to expand or contract.

* * * * *